United States Patent
Tian et al.

(10) Patent No.: US 11,931,135 B1
(45) Date of Patent: Mar. 19, 2024

(54) HUMAN-SCALE CLOSED-BORE MPI DEVICE BASED ON RADIAL-CARTESIAN TRAJECTORY SCANNING

(71) Applicant: Beijing University of Aeronautics and Astronautics, Beijing (CN)

(72) Inventors: Jie Tian, Beijing (CN); Jie He, Beijing (CN); Bo Zhang, Beijing (CN); Yu An, Beijing (CN)

(73) Assignee: Beijing University of Aeronautics and Astronautics, Beijing (CN)

( * ) Notice: Subject to any disclaimer, the term of this patent is extended or adjusted under 35 U.S.C. 154(b) by 0 days.

(21) Appl. No.: 18/384,362

(22) Filed: Oct. 26, 2023

(30) Foreign Application Priority Data

Feb. 7, 2023 (CN) .......................... 202310070548.2

(51) Int. Cl.
  *A61B 5/0515* (2021.01)
  *G01R 33/12* (2006.01)

(52) U.S. Cl.
  CPC ........ *A61B 5/0515* (2013.01); *G01R 33/1276* (2013.01)

(58) Field of Classification Search
  CPC .......................... A61B 5/0515; G01R 33/1276
  See application file for complete search history.

(56) References Cited

U.S. PATENT DOCUMENTS

| 2011/0089942 A1 | 4/2011 | Goodwill et al. |
| 2018/0017641 A1* | 1/2018 | Goodwill ........... G01R 33/0213 |
| 2020/0289839 A1* | 9/2020 | Hensley ............... A61B 5/0515 |

FOREIGN PATENT DOCUMENTS

| CN | 113331812 A | 9/2021 | |
| CN | 113397521 A | 9/2021 | |
| CN | 114521883 A | 5/2022 | |
| CN | 115120222 A | 9/2022 | |
| DE | 102020202097 B3 * | 4/2021 | ......... G01R 33/1276 |
| WO | WO-2023042265 A1 * | 3/2023 | |

OTHER PUBLICATIONS

Knopp et al., Efficient generation of a magnetic field-free line. Med Phys. Jul. 2010;37(7):3538-40 (Year: 2010).*

* cited by examiner

*Primary Examiner* — Daniel R Miller
(74) *Attorney, Agent, or Firm* — Bayramoglu Law Offices LLC (57) ABSTRACT

A human-scale closed-bore MPI device and method based on radial-Cartesian trajectory scanning are provided. The human-scale closed-bore MPI device includes: a gradient module configured to generate a static gradient magnetic field; a rotating scanning module configured to construct a rotating uniform alternating magnetic field; an excitation module configured to construct a uniform alternating magnetic field; an induction module configured to acquire a nonlinear magnetization response signal of magnetic particles; and a compensation module configured to compensate for a coupling signal between a first cylindrical coil and a second cylindrical coil.

8 Claims, 6 Drawing Sheets

HUMAN-SCALE CLOSED-BORE MPI DEVICE BASED ON RADIAL-CARTESIAN TRAJECTORY SCANNING

CROSS REFERENCE TO THE RELATED APPLICATIONS

This application is based upon and claims priority to Chinese Patent Application No. 202310070548.2, filed on Feb. 7, 2023, the entire contents of which are incorporated herein by reference.

TECHNICAL FIELD

The present disclosure belongs to the technical field of magnetic particle imaging (MPI), and particularly relates to a human-scale closed-bore MPI device and method based on radial-Cartesian trajectory scanning.

BACKGROUND

Magnetic particle imaging (MPI) is a tracer-based imaging method that can measure the concentration of superparamagnetic iron oxide (SPIO) nanoparticles. These particles are usually delivered intravenously to image the vascular system and organ perfusion. In terms of application, MPI has been proven to be able to detect ischemic stroke in mouse models, with high sensitivity and temporal resolution, and to be suitable for imaging of intestinal bleeding, lung perfusion, labeled stem cells, cerebral aneurysms, cancer, and cerebral blood volume. In addition, MPI has also been proven to be a very useful tool in interventional applications, and it can even be used for catheter diversion.

The main obstacle to the application of MPI at the human scale is the lack of an imaging device with a sufficient bore size. The bore size of most existing MPI systems is 3-40 cm, which can only accommodate mice, rats, and human heads. Scaling of the MPI imaging hardware to image the whole human body poses a challenge to the excitation and reception coils, as a larger imaging volume requires larger inductance, transmission power, and physical size.

To reduce the size and power consumption of the human-scale MPI device, the present disclosure proposes a human-scale closed-bore MPI device and method based on radial-Cartesian trajectory scanning of a field-free point.

SUMMARY

The present disclosure aims to solve the above-mentioned problem in the prior art that the existing magnetic particle imaging (MPI) device has small bores and cannot image a large-sized target object (such as the whole human body). For this purpose, the present disclosure proposes a human-scale closed-bore MPI device based on radial-Cartesian trajectory scanning, including a gradient module, a rotating scanning module, an excitation module, an induction module, and a compensation module, where the gradient module includes two circular permanent magnets; the two circular permanent magnets are identically shaped, parallel to each other, and provided with central axes that are collinear; and the gradient module is configured to generate a static gradient magnetic field;

the rotating scanning module includes two curved rectangular coils; the two curved rectangular coils are arranged between the two circular permanent magnets, and are mirrored about a first plane; and the first plane includes the central axes of the two circular permanent magnets;

the rotating scanning module is configured to construct a rotating uniform alternating magnetic field to control a field-free point to make translational reciprocating motion along a radial direction of an imaging hole and rotational motion along an axial direction of the imaging hole; the axial direction of the imaging hole is parallel to a direction of the central axes of the two circular permanent magnets; and the radial direction of the imaging hole is perpendicular to the axial direction of the imaging hole;

the excitation module includes a cylindrical coil serving as a first cylindrical coil; the first cylindrical coil is nested inside the two curved rectangular coils and the two circular permanent magnets; and the excitation module is configured to construct a uniform alternating magnetic field;

the two curved rectangular coils are tightly adhered to a first cylindrical surface; a diameter of the first cylindrical surface is smaller than an inner diameter of the two circular permanent magnets and greater than an outer diameter of the first cylindrical coil;

the induction module includes a cylindrical coil serving as a second cylindrical coil; the second cylindrical coil is nested inside the first cylindrical coil; and the induction module is configured to acquire a nonlinear magnetization response signal of magnetic particles;

the compensation module includes two cylindrical coils that serve as a third cylindrical coil and a fourth cylindrical coil, respectively; the fourth cylindrical coil is nested inside the third cylindrical coil; the third cylindrical coil is connected in series with the first cylindrical coil; the fourth cylindrical coil is connected in series with the second cylindrical coil; and the compensation module is configured to compensate for a coupling signal between the first cylindrical coil and the second cylindrical coil;

the compensation module is located outside the gradient module; and a spatial distance between the compensation module and the gradient module, as well as the rotating scanning module, the excitation module, and the induction module is greater than a set distance threshold; and the first cylindrical coil, the second cylindrical coil, the third cylindrical coil, and the fourth cylindrical coil are coaxial with the central axes of the two circular permanent magnets.

In some preferred implementations, the human-scale closed-bore MPI device based on radial-Cartesian trajectory scanning further includes a circuit system, a mechanical rotation device, an examination bed, a cooling system, an imaging module, and a control device; and the circuit system, the mechanical rotation device, the examination bed, the cooling system, and the imaging module are all signal-connected with the control device;

the circuit system is configured to supply power and perform sampling for a scanning imaging component; and the scanning imaging component is a scanning imaging system including the gradient module, the rotating scanning module, the excitation module, the induction module, and the compensation module;

the mechanical rotation device is configured to perform mechanical rotation of a rotating scanning coil in the scanning imaging component;

the examination bed is configured to carry an examination object and move along the axial direction of the imaging hole to a preset position;

the cooling system is configured to absorb heat generated by the scanning imaging component in operation;

the imaging module is configured to reconstruct a spatial distribution image of a physical feature of the magnetic particles; and the control device is configured to control, according to set control instructions, current changes of the two rotating scanning coils and an excitation coil of the scanning imaging component, a mechanical rotation speed of the two rotating scanning coils of the scanning imaging component, a depth of movement of the examination bed, and a hydraulic pressure of the cooling system, such that the field-free point performs layer-by-layer scanning through translation and rotation, thereby achieving scanning imaging of the examination object.

In some preferred implementations, the human-scale closed-bore MPI device based on radial-Cartesian trajectory scanning takes the direction of the central axes of the two circular permanent magnets as an x direction and a longitudinal direction of a central axis of the cylindrical coil as a z direction.

In some preferred implementations, residual magnetization directions of the two circular permanent magnets are opposite to each other and parallel to the central axes of the two circular permanent magnets.

In some preferred implementations, output voltage phases of the third cylindrical coil and the fourth cylindrical coil are opposite.

A second aspect of the present disclosure proposes a human-scale closed-bore MPI method based on radial-Cartesian trajectory scanning, implemented through the human-scale closed-bore MPI device based on radial-Cartesian trajectory scanning, and including:

S100: moving the examination object along the axial direction of the imaging hole to the preset position;

S200: constructing, based on the two circular permanent magnets, the two curved rectangular coils, and the first cylindrical coil, the field-free point and a dynamic magnetic field for radial-Cartesian trajectory scanning;

S300: acquiring, based on the second cylindrical coil, the third cylindrical coil, and the fourth cylindrical coil, the nonlinear magnetization response signal of the magnetic particles;

S400: reconstructing, based on the acquired nonlinear magnetization response signal of the magnetic particles, the spatial distribution image of the physical feature of the magnetic particles through a preset imaging algorithm; and S500: moving the examination object along the axial direction of the imaging hole, and repeating steps S200 to S400 until the imaging of all examination regions of the examination object is completed.

In some preferred implementations, the constructing, based on the two circular permanent magnets, the two curved rectangular coils, and the first cylindrical coil, the field-free point and a dynamic magnetic field for radial-Cartesian trajectory scanning includes:

keeping the two circular permanent magnets and the first cylindrical coil fixed; controlling the two curved rectangular coils to rotate uniformly and mechanically around the central axes of the two circular permanent magnets; and applying alternating currents of same magnitude and direction to the two curved rectangular coils; and applying an alternating current to the first cylindrical coil;

where, a frequency of the alternating current applied to the first cylindrical coil is at least N times a frequency of the alternating current applied to the two curved rectangular coils; and the frequency of the alternating current applied to the two curved rectangular coils is at least N times a mechanical rotation frequency of the two curved rectangular coils.

In some preferred implementations, the acquiring, based on the second cylindrical coil, the third cylindrical coil, and the fourth cylindrical coil, the nonlinear magnetization response signal of the magnetic particles includes: connecting the second cylindrical coil and the fourth cylindrical coil in series to output a voltage signal for filtering, noise reduction, and amplification, thereby acquiring the nonlinear magnetization response signal of the magnetic particles.

The present disclosure has following beneficial effects:

The present disclosure achieves MPI of a large-sized target object and has the advantages of simple structure, high space utilization, and low power consumption.

In the present disclosure, the permanent magnets generate a gradient magnetic field, the mechanically rotating scanning coil applied with an alternating current generates a rotating scanning magnetic field, and the cylindrical coil generates an excitation field. The examination object is moved to achieve segmented scanning and imaging of the human body, thereby ultimately achieving whole-body MPI. The present disclosure reduces the size and power consumption of the human-scale MPI device, and has the advantages of simple structure, high space utilization, and low power consumption.

BRIEF DESCRIPTION OF THE DRAWINGS

Other features, objectives and advantages of the present disclosure will become more apparent upon reading the detailed description of the non-restrictive embodiments made below with reference to the drawings.

REFERENCE NUMERALS 1. circular permanent magnet; 2. curved rectangular coil; 3. first cylindrical coil; 4. second cylindrical coil; 5. third cylindrical coil; 6. fourth cylindrical coil; 7. circuit system of human-scale closed-bore magnetic particle imaging (MPI) device based on radial-Cartesian trajectory scanning of field-free point; 8. mechanical rotation system of human-scale closed-bore MPI device based on radial-Cartesian trajectory scanning of field-free point 9. mechanical displacement system of examination bed; 10. examination bed; 11. examination object; 12. water cooling system; 13. control device; 14. display device; and 15. image processing device.

DETAILED DESCRIPTION OF THE EMBODIMENTS

In order to make the objectives, technical solutions, and advantages of the embodiments of the present disclosure clearer, the technical solutions in the embodiments of the present disclosure will be clearly and completely described below in conjunction with the drawings in the embodiments of the present disclosure. Apparently, the described embodiments are some, rather than all of the embodiments of the present disclosure. All other embodiments obtained by those skilled in the art based on the embodiments of the present disclosure without creative efforts shall fall within the protection scope of the present disclosure.

The present disclosure will be further described in detail below in conjunction with the drawings and embodiments. It may be understood that the specific embodiments described herein are merely intended to explain the related invention, rather than to limit the present disclosure. It should be noted that the embodiments in the present disclosure and features in the embodiments may be combined with each other in a non-conflicting situation.

Figure 1:
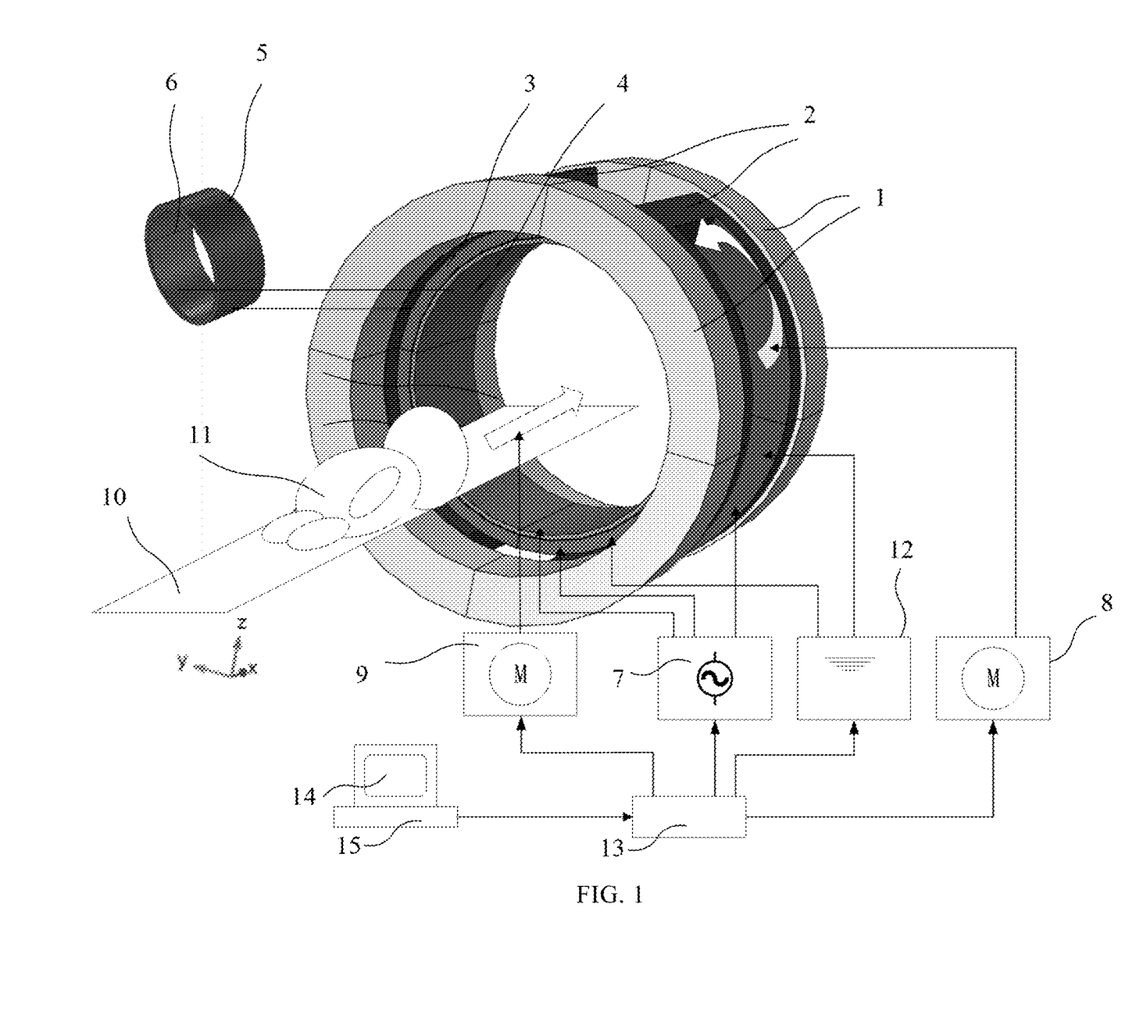
FIG. 1 is a three-dimensional structural diagram of a human-scale closed-bore magnetic particle imaging (MPI) device based on radial-Cartesian trajectory scanning according to an embodiment of the present disclosure.
Figure 2:
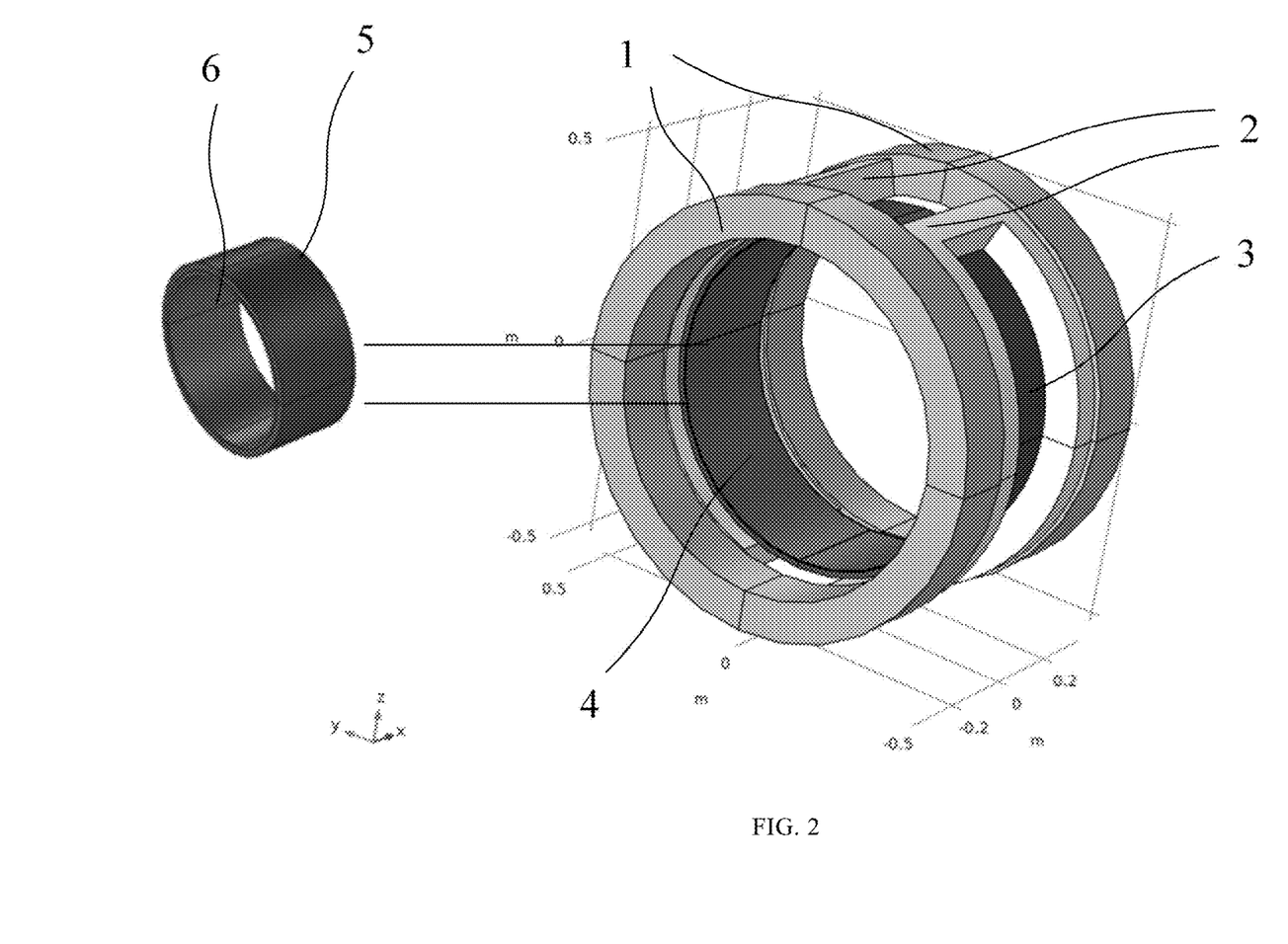
FIG. 2 is a structural diagram of a scanning imaging component according to an embodiment of the present disclosure.

A first embodiment of the present disclosure proposes a human-scale closed-bore MPI device based on radial-Cartesian trajectory scanning. As shown in FIGS. 1 and 2, the human-scale closed-bore MPI device includes a gradient module, a rotating scanning module, an excitation module, an induction module, and a compensation module.

The gradient module includes two circular permanent magnets. The two circular permanent magnets are identically shaped, parallel to each other, and provided with central axes that are collinear. The gradient module is configured to generate a static gradient magnetic field.

The rotating scanning module includes two curved rectangular coils. The two curved rectangular coils are arranged between the two circular permanent magnets, and are mirrored about a first plane. The first plane includes the central axes of the two circular permanent magnets.

The rotating scanning module is configured to construct a rotating uniform alternating magnetic field to control a field-free point to make translational reciprocating motion along a radial direction of an imaging hole and rotational motion along an axial direction of the imaging hole. The axial direction of the imaging hole is parallel to a direction of the central axes of the two circular permanent magnets, and the radial direction of the imaging hole is perpendicular to the axial direction of the imaging hole.

The excitation module includes a cylindrical coil serving as a first cylindrical coil. The first cylindrical coil is nested inside the two curved rectangular coils and the two circular permanent magnets. The excitation module is configured to construct a uniform alternating magnetic field.

The two curved rectangular coils are tightly adhered to a first cylindrical surface. A diameter of the first cylindrical surface is smaller than an inner diameter of the two circular permanent magnets and greater than an outer diameter of the first cylindrical coil.

The induction module includes a cylindrical coil serving as a second cylindrical coil. The second cylindrical coil is nested inside the first cylindrical coil. The induction module is configured to acquire a nonlinear magnetization response signal of magnetic particles.

The compensation module includes two cylindrical coils that serve as a third cylindrical coil and a fourth cylindrical coil, respectively. The fourth cylindrical coil is nested inside the third cylindrical coil. The third cylindrical coil is connected in series with the first cylindrical coil. The fourth cylindrical coil is connected in series with the second cylindrical coil. The compensation module is configured to compensate for a coupling signal between the first cylindrical coil and the second cylindrical coil.

The compensation module is located outside the gradient module. A spatial distance between the compensation module and the gradient module, as well as the rotating scanning module, the excitation module, and the induction module is greater than a set distance threshold.

The first cylindrical coil, the second cylindrical coil, the third cylindrical coil, and the fourth cylindrical coil are coaxial with the central axes of the two circular permanent magnets.

To more clearly explain the human-scale closed-bore MPI device based on radial-Cartesian trajectory scanning in the embodiment of the present disclosure, modules of the device are described in detail below with reference to the drawings.

The present disclosure provides a human-scale closed-bore MPI device based on radial-Cartesian trajectory scanning. As shown in FIG. 1, the human-scale closed-bore MPI device includes a scanning imaging component (i.e. a scanning imaging system including a gradient module, a rotating scanning module, an excitation module, an induction module, and a compensation module), circuit system 7, mechanical rotation device (i.e. mechanical rotation system 8 shown in FIG. 1), examination bed 10, cooling system (i.e. water cooling system 12 shown in FIG. 1), an imaging module (including display device 14 and image processing device 15 shown in FIG. 1), and control device 13. The scanning imaging component, the circuit system 7, the mechanical rotation device, the examination bed 10, the water cooling system 12, and the imaging module are all signal-connected (i.e. communicated) with the control device 13. Specifically:

The gradient module includes two circular permanent magnets (i.e., circular permanent magnets 1). As shown in FIG. 2, the two circular permanent magnets are identically shaped, parallel to each other, and provided with central axes that are collinear. The gradient module is configured to generate a static gradient magnetic field to saturate magnetic nanoparticles far from a field-free line. Residual magnetization directions of the two circular permanent magnets 1 are opposite to each other and parallel to the central axes of the two circular permanent magnets.

The rotating scanning module includes two curved rectangular coils (i.e., curved rectangular coils 2), as shown in FIGS. 1 and 2. For a distinguishing purpose, the color of the curved rectangular coils 2 is modified. The two curved rectangular coils 2 are arranged between the two circular permanent magnets 1. The two curved rectangular coils 2 are specifically minor arcs with a length less than that of a semi-circle, and are mirrored about a first plane. The first plane includes the central axes of the two circular permanent magnets 1.

The human-scale closed-bore MPI device based on radial-Cartesian trajectory scanning takes the direction of the central axes of the two circular permanent magnets as an x direction and a longitudinal direction of a central axis of the cylindrical coil as a z direction. That is, the first plane is mirrored to an xz plane, as shown in FIG. 1.

the rotating scanning module is configured to construct a rotating uniform alternating magnetic field to control a field-free point to make translational reciprocating motion along a radial direction of an imaging hole and rotational motion along an axial direction of the imaging hole; the axial direction of the imaging hole is parallel to a direction of the central axes of the two circular permanent magnets; and the radial direction of the imaging hole is perpendicular to the axial direction of the imaging hole;

The excitation module includes a cylindrical coil serving as first cylindrical coil 3. The first cylindrical coil 3 is nested inside the two curved rectangular coils and the two circular permanent magnets 1. The excitation module is configured to construct a uniform alternating magnetic field, so as to excite the magnetic particles to make a nonlinear magnetization response.

The two curved rectangular coils 2 are tightly adhered to a first cylindrical surface. A diameter of the first cylindrical surface is smaller than an inner diameter of the two circular permanent magnets 1 and greater than an outer diameter of the first cylindrical coil 3.

The induction module includes a cylindrical coil serving as second cylindrical coil 4. The second cylindrical coil 4 is nested inside the first cylindrical coil 3. The induction module is configured to acquire a nonlinear magnetization response signal of the magnetic particles.

The compensation module includes two cylindrical coils that serve as third cylindrical coil 5 and fourth cylindrical coil 6, respectively. The fourth cylindrical coil 6 is nested inside the third cylindrical coil 5. The third cylindrical coil 5 and the fourth cylindrical coil 6 are only connected with the first cylindrical coil 3 and the second cylindrical coil 4 through a cable. The third cylindrical coil 5 is connected in series with the first cylindrical coil 3, and the fourth cylindrical coil 6 is connected in series with the second cylindrical coil 4. Output voltage phases of the third cylindrical coil 5 and the fourth cylindrical coil 6 are opposite. The compensation module is configured to compensate for a coupling signal between the first cylindrical coil 3 and the second cylindrical coil 4.

The compensation module is located outside the gradient module. As shown in FIG. 1, a spatial distance between the compensation module and the gradient module, as well as the rotating scanning module, the excitation module, and the induction module is greater than a set distance threshold. That is, the compensation module is spatially far away from the gradient module, the rotating scanning module, the excitation module, and the induction module. Therefore, the compensation module is not affected by the magnetic field spatial coupling of the gradient module, the rotating scanning module, the excitation module, and the induction module.

The first cylindrical coil 3, the second cylindrical coil 4, the third cylindrical coil 5, and the fourth cylindrical coil 6 are coaxial with the central axes of the two circular permanent magnets 1.

The circuit system 7 is configured to supply power and perform sampling for the scanning imaging component. The scanning imaging component is a scanning imaging system including the gradient module, the rotating scanning module, the excitation module, the induction module, and the compensation module.

The mechanical rotation device is configured to perform mechanical rotation of a rotating scanning coil in the scanning imaging component.

The examination bed 10 is configured to carry an examination object 11 and move along the axial direction of the imaging hole to a preset position.

The cooling system is configured to absorb heat generated by the scanning imaging component in operation.

The imaging module is configured to reconstruct a spatial distribution image of a physical feature of the magnetic particles.

The control device 13 is configured to control, according to set control instructions, current changes of the two rotating scanning coils and an excitation coil of the scanning imaging component, a mechanical rotation speed of the two rotating scanning coils of the scanning imaging component, a depth of movement of the examination bed, and a hydraulic pressure of the cooling system, such that the field-free point performs layer-by-layer scanning through translation and rotation, thereby achieving scanning imaging of the examination object.

Figure 5:
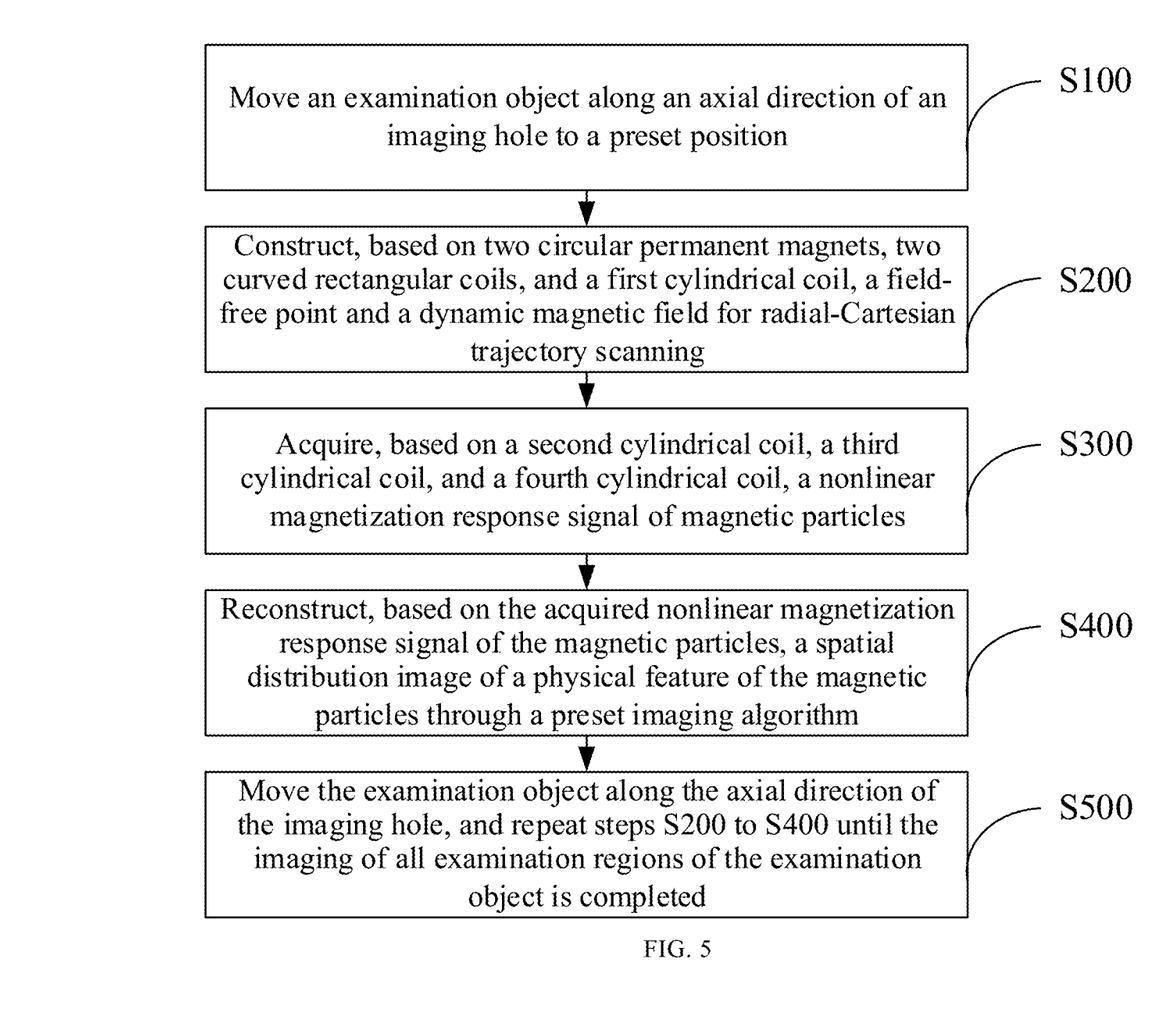
FIG. 5 is a flowchart of a human-scale closed-bore MPI method based on radial-Cartesian trajectory scanning according to an embodiment of the present disclosure.

A second embodiment of the present disclosure proposes a human-scale closed-bore MPI method based on radial-Cartesian trajectory scanning, as shown in FIG. 5. The human-scale closed-bore MPI method is based on the human-scale closed-bore MPI device based on radial-Cartesian trajectory scanning, and includes the following steps.

S100. The examination object is moved along the axial direction of the imaging hole to the preset position.

In this embodiment, the examination object is first moved along the axial direction of the imaging hole to the preset position.

S200. Based on the two circular permanent magnets, the two curved rectangular coils, and the first cylindrical coil, the field-free point and a dynamic magnetic field are constructed for radial-Cartesian trajectory scanning.

Figure 3:
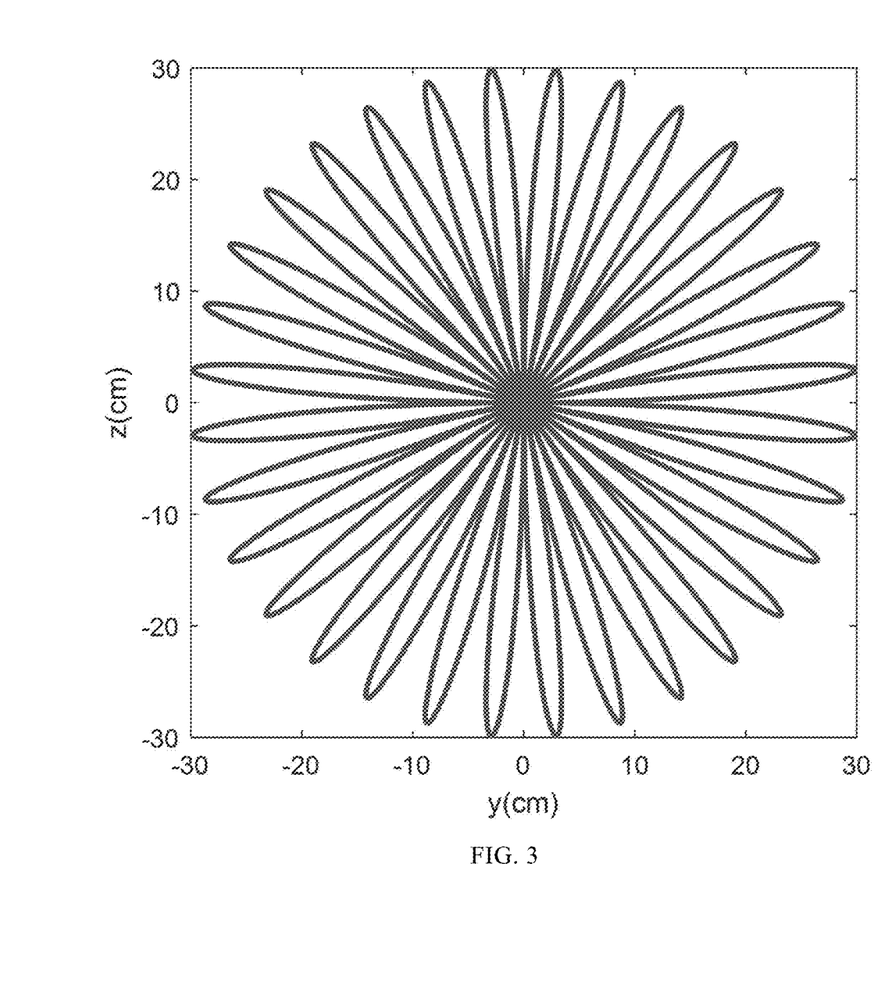
FIG. 3 is a schematic diagram of projection of a radial-Cartesian trajectory on a transverse section of an imaging hole according to an embodiment of the present disclosure.
Figure 4:
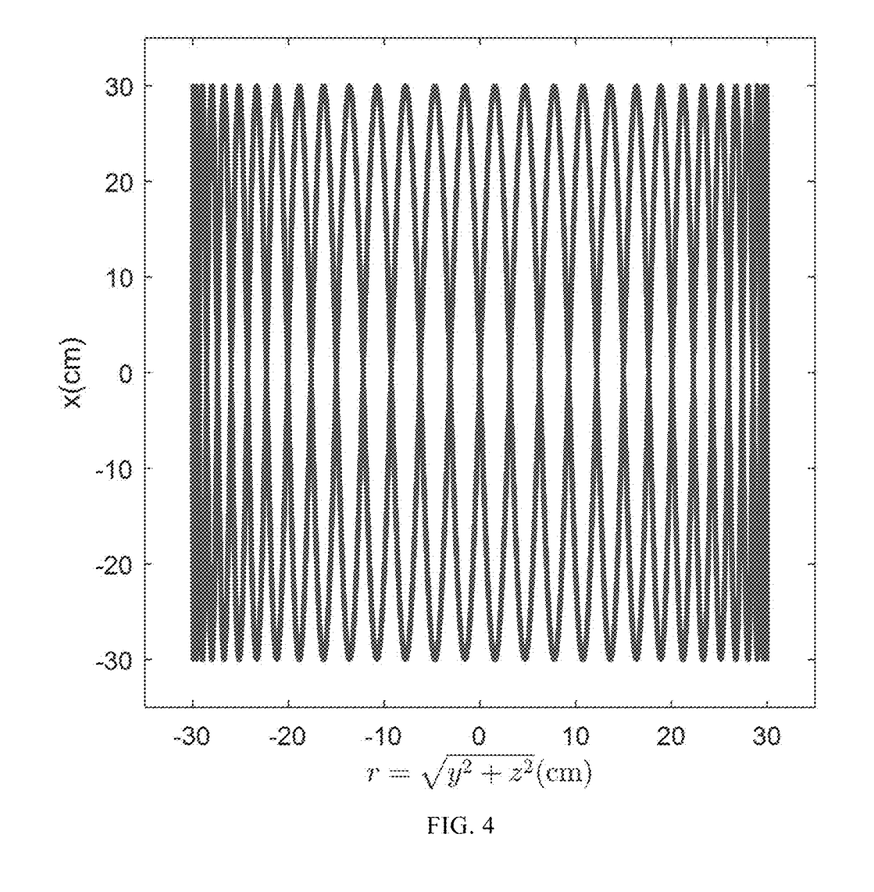
FIG. 4 is a schematic diagram of the projection of the radial-Cartesian trajectory on an axial section of an imaging hole according to an embodiment of the present disclosure.

In the present disclosure, the projection of the scanning trajectory on the transverse section of the imaging hole is a radial trajectory, while the projection of the scanning trajectory on the axial section of the imaging hole is a Cartesian trajectory, so the scanning trajectory is called a radial-Cartesian trajectory. In this embodiment, the field-free point and the dynamic magnetic field for radial-Cartesian trajectory scanning are constructed as follows.

The two circular permanent magnets and the first cylindrical coil are kept fixed. The two curved rectangular coils are controlled to rotate uniformly and mechanically around the central axes of the two circular permanent magnets. Alternating currents of same magnitude and direction are applied to the two curved rectangular coils, and an alternating current is applied to the first cylindrical coil.

A frequency of the alternating current applied to the first cylindrical coil is at least N times a frequency of the alternating current applied to the two curved rectangular coils. The frequency of the alternating current applied to the two curved rectangular coils is at least N times a mechanical rotation frequency of the two curved rectangular coils. In the present disclosure, N is preferably 10. In addition, the projection of the radial-Cartesian trajectory on the transverse section of the imaging hole and the projection of the radial-Cartesian trajectory on the axial section of the imaging hole are shown in FIGS. 3 and 4. In FIG. 4, $r=\sqrt{y^2+z^2}$ refers to a distance between the field-free point and the central axis of the imaging hole.

S300. Based on the second cylindrical coil, the third cylindrical coil, and the fourth cylindrical coil, the nonlinear magnetization response signal of the magnetic particles is acquired.

In this embodiment, the nonlinear magnetization response signal of the magnetic particles is acquired as follows.

The second cylindrical coil and the fourth cylindrical coil are connected in series to output a voltage signal for filtering, noise reduction, and amplification, thereby acquiring the nonlinear magnetization response signal of the magnetic particles.

S400. Based on the acquired nonlinear magnetization response signal of the magnetic particles, the spatial distribution image of the physical feature of the magnetic particles is reconstructed through a preset imaging algorithm.

In this embodiment, the preset imaging algorithm is preferably a system matrix-based MPI reconstruction algorithm or an x space-based MPI reconstruction algorithm. In other embodiments, it can be selected according to actual needs.

S500. The examination object is moved along the axial direction of the imaging hole, and steps S200 to S400 are repeated until the imaging of all examination regions of the examination object is completed.

A third embodiment of the present disclosure proposes a human-scale closed-bore MPI system based on radial-Cartesian trajectory scanning. The human-scale closed-bore MPI system includes a moving module, a trajectory scanning module, a signal acquisition module, an image reconstruction module, and a repetition module.

The moving module is configured to move the examination object along the axial direction of the imaging hole to the preset position.

The trajectory scanning module is configured to construct, based on the two circular permanent magnets, the two curved rectangular coils, and the first cylindrical coil, the field-free point and a dynamic magnetic field for radial-Cartesian trajectory scanning.

The signal acquisition module is configured to acquire, based on the second cylindrical coil, the third cylindrical coil, and the fourth cylindrical coil, the nonlinear magnetization response signal of the magnetic particles.

The image reconstruction module is configured to reconstruct, based on the acquired nonlinear magnetization response signal of the magnetic particles, the spatial distribution image of the physical feature of the magnetic particles is reconstructed through a preset imaging algorithm.

The repetition module is configured to move the examination object along the axial direction of the imaging hole, and repeat operation steps of the trajectory scanning module, the signal acquisition module, and the image reconstruction module until the imaging of all examination regions of the examination object is completed.

Those skilled in the art should clearly understand that, for convenience and brevity of description, reference is made to corresponding processes in the above method embodiments for specific working processes of the system, and details are not described herein again.

It should be noted that the human-scale closed-bore magnetic particle imaging (MPI) device/system based on radial-Cartesian trajectory scanning in the above embodiments is only described by taking the division of the above functional modules as an example. In practical applications, the above functions can be completed by different functional modules as required, that is, the modules or steps in the embodiments of the present disclosure are further decomposed or combined. For example, the modules in the above embodiments may be combined into one module, or may be further divided into a plurality of sub-modules to complete all or part of the functions described above. The names of the modules and steps involved in the embodiments of the present disclosure are only for distinguishing each module or step, and should not be regarded as improper limitations on the present disclosure.

A fourth embodiment of the present disclosure provides an electronic device, including: at least one processor and a memory communicatively connected with the at least one processor, where the memory stores an instruction executable by the processor; and the instruction is executed by the processor to implement the above human-scale closed-bore MPI method based on radial-Cartesian trajectory scanning.

A fifth embodiment of the present disclosure proposes a computer-readable storage medium, which stores a computer instruction, where the computer instruction is executed by a computer to implement the above human-scale closed-bore MPI method based on radial-Cartesian trajectory scanning.

Those skilled in the art can clearly understand that, for convenience and brevity of description, reference can be made to a corresponding process in the above method embodiment for specific working processes and related descriptions of the above electronic device and computer-readable storage medium. Details are not described herein again.

Figure 6:
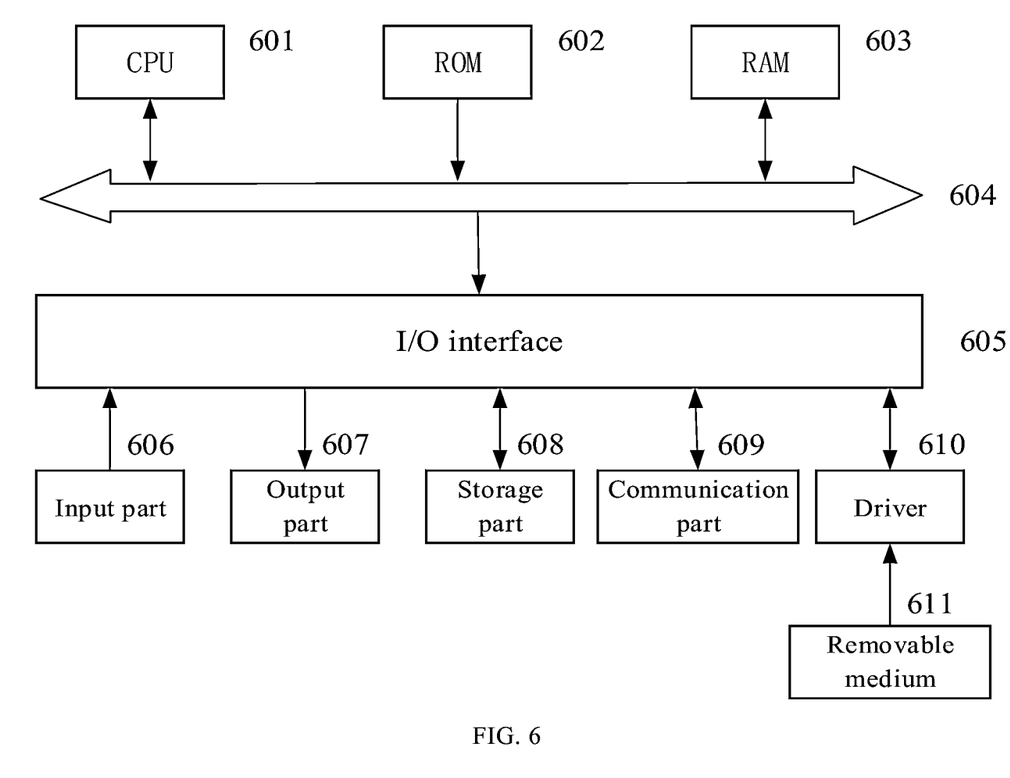
FIG. 6 is a structural diagram of a computer system of an electronic device for implementing the human-scale closed-bore MPI method based on radial-Cartesian trajectory scanning according to an embodiment of the present disclosure.

FIG. 6 shows a structural diagram of a computer system of a server suitable for implementing the method, system and device embodiments of the present disclosure. The server shown in FIG. 6 is merely an example, and should not be conceived as any limitation to the functions and application range of the embodiments of the present disclosure.

As shown in FIG. 6, the computer system includes a central processing unit (CPU) 601, which can perform various suitable actions and processing according to a program in a read-only memory (ROM) 602 or a program loaded from a storage part 608 to a random access memory (RAM) 603. The RAM 603 further stores various programs and data required for operations of the system. The CPU 601, the ROM 602 and the RAM 603 are connected to each other through a bus 604. An input/output (I/O) interface 605 is connected to the bus 604.

The following components are connected to the I/O interface 605: an input part 606 including a keyboard, a mouse, and the like; an output part 607 including a liquid crystal display (LCD), a loudspeaker, and the like; the storage part 608 including a hard disk; and a communication part 609 including a network interface card such as a local area network (LAN) card or a modem. The communication part 609 executes communication processing via a network such as the Internet. A driver 610 may also be connected to the I/O interface 605 as required. A removable medium 611, such as a magnetic disk, an optical disc, a magneto-optical disc, a semiconductor memory, or the like, is installed on the driver 610 as required, so that a computer program read therefrom can be installed in the storage part 608 as required.

Particularly, according to the embodiments of the present disclosure, the process described above with reference to the flowchart may be implemented as a computer software program. For example, an embodiment of the present disclosure includes a computer program product including a computer program carried by a computer-readable medium. The computer program includes program code for executing the method shown in the flowchart. In this embodiment, the computer program may be downloaded from a network by means of the communication part 609, and/or be downloaded from a removable medium 611. When the computer program is executed by the CPU 601, the functions defined in the method of the present disclosure are executed. It should be noted that, the computer-readable medium in the present disclosure may be a computer-readable signal medium, a computer-readable storage medium, or a combination thereof. The computer readable storage medium, may be, for example, but not limited to, electrical, magnetic, optical, electromagnetic, infrared, or semiconductor systems, apparatuses, or devices, or any combination thereof. More specific examples of the computer readable storage medium may include, but are not limited to: an electrical connection with one or more conducting wires, a portable computer disk, a hard disk, a RAM, a ROM, an erasable programmable ROM (an EPROM or a flash memory), an optical fiber, a portable compact disk read-only memory (CD-ROM), an optical storage device, a magnetic storage device, or any suitable combination thereof. In the present disclosure, the computer readable storage medium may be any tangible medium including or storing a program, and the program may be used by or used in combination with an instruction execution system, apparatus or device. In the present disclosure, the computer readable signal medium may include a data signal propagated in a baseband or propagated as a part of a carrier, and carries a computer readable program code. The propagated data signal may be in various forms, including but not limited to an electromagnetic signal, an optical signal, or any suitable combination thereof. The computer-readable signal medium may alternatively be any computer-readable medium except the computer-readable storage medium. The computer-readable medium may send, propagate or transmit a program used by or used in combination with an instruction execution system, apparatus or device. The program code contained on the computer readable medium may be transmitted using any suitable medium, including but not limited to: wireless, wire, optical fiber, RF, or any suitable combination thereof.

The computer program code for executing the operations in the present disclosure may be compiled by using one or more program design languages or a combination thereof. The programming languages include object oriented programming languages, such as Java, Smalltalk, and C++, and conventional procedural programming languages, such as C or similar programming languages. The program code may be executed fully on a user computer, executed partially on a user computer, executed as an independent software package, executed partially on a user computer and partially on a remote computer, or executed fully on a remote computer or a server. In a circumstance in which a remote computer is involved, the remote computer may be connected to a user computer over any type of network, including a local area network (LAN) or a wide area network (WAN), or may be connected to an external computer (for example, connected over the Internet by using an Internet service provider).

The flowcharts and block diagrams in the accompanying drawings illustrate system architectures, functions and operations that may be implemented by the system, method and computer program product according to the embodiments of the present disclosure. In this regard, each block in the flowcharts or block diagrams may represent a module, a program segment or a part of code, and the module, the program segment or the part of code includes one or more executable instructions for implementing specified logic functions. It should also be noted that, in some alternative implementations, the functions marked in the blocks may alternatively occur in a different order from that marked in the drawings. For example, two successively shown blocks actually may be executed in parallel substantially, or may be executed in reverse order sometimes, depending on the functions involved. It should also be noted that each block in the flowcharts and/or block diagrams and combinations of the blocks in the flowcharts and/or block diagrams may be implemented by a dedicated hardware-based system for executing specified functions or operations, or may be implemented by a combination of dedicated hardware and computer instructions.

Terms such as "first" and "second" are intended to distinguish between similar objects, rather than describe or indicate a specific order or sequence.

Terms "include", "comprise" or any other variations thereof are intended to cover non-exclusive inclusions, so that a process, a method, an article, or a device/apparatus including a series of elements not only includes those elements, but also includes other elements that are not explicitly listed, or also includes inherent elements of the process, the method, the article or the device/apparatus.

The technical solutions of the present disclosure are described in the preferred implementations with reference to the drawings. Those skilled in the art should easily understand that the protection scope of the present disclosure is apparently not limited to these specific implementations. Those skilled in the art can make equivalent changes or substitutions to the relevant technical features without departing from the principles of the present disclosure, and the technical solutions after these changes or substitutions should fall within the protection scope of the present disclosure.

What is claimed is:

1. A human-scale closed-bore magnetic particle imaging (MPI) device based on a radial-Cartesian trajectory scanning, comprising a gradient module, a rotating scanning module, a mechanical rotation device, an excitation module, an induction module, and a compensation module, wherein the gradient module comprises two circular permanent magnets; the two circular permanent magnets are identically shaped, parallel to each other, and provided with central axes that are collinear; and the gradient module is configured to generate a static gradient magnetic field;

the rotating scanning module comprises two curved rectangular coils; the two curved rectangular coils are arranged between the two circular permanent magnets, and are mirrored about a first plane; and the first plane comprises the central axes of the two circular permanent magnets;

the mechanical rotation device is configured to perform mechanical rotation of the rotating scanning module;

the rotating scanning module and the mechanical rotation device are configured to construct a rotating uniform alternating magnetic field to control a field-free point to make translational reciprocating motion along a radial direction of an imaging hole and rotational motion along an axial direction of the imaging hole; the axial direction of the imaging hole is parallel to a direction of the central axes of the two circular permanent magnets; and the radial direction of the imaging hole is perpendicular to the axial direction of the imaging hole;

the excitation module comprises a cylindrical coil serving as a first cylindrical coil; the first cylindrical coil is nested inside the two curved rectangular coils and the two circular permanent magnets; and the excitation module is configured to construct a uniform alternating magnetic field;

the two curved rectangular coils are tightly adhered to a first cylindrical surface; a diameter of the first cylindrical surface is smaller than an inner diameter of the two circular permanent magnets and greater than an outer diameter of the first cylindrical coil;

the induction module comprises a cylindrical coil serving as a second cylindrical coil; the second cylindrical coil is nested inside the first cylindrical coil; and the induction module is configured to acquire a nonlinear magnetization response signal of magnetic particles;

the compensation module comprises two cylindrical coils that serve as a third cylindrical coil and a fourth cylindrical coil, respectively; the fourth cylindrical coil is nested inside the third cylindrical coil; the third cylindrical coil is connected in series with the first cylindrical coil; the fourth cylindrical coil is connected in series with the second cylindrical coil; and the compensation module is configured to compensate for a coupling signal between the first cylindrical coil and the second cylindrical coil;

the compensation module is located outside the gradient module; and a spatial distance between the compensation module and the gradient module, as well as the rotating scanning module, the excitation module, and the induction module is greater than a set distance threshold; and the first cylindrical coil, the second cylindrical coil, the third cylindrical coil, and the fourth cylindrical coil are coaxial with the central axes of the two circular permanent magnets.

2. The human-scale closed-bore MPI device based on the radial-Cartesian trajectory scanning according to claim 1, further comprising a circuit system, an examination bed, a cooling system, an imaging module, and a control device, wherein the circuit system, the mechanical rotation device, the examination bed, the cooling system, and the imaging module are all signal-connected with the control device;

the circuit system is configured to supply power and perform sampling for a scanning imaging component; and the scanning imaging component is a scanning imaging system comprising the gradient module, the rotating scanning module, the excitation module, the induction module, and the compensation module;

the examination bed is configured to carry an examination object and move along the axial direction of the imaging hole to a preset position;

the cooling system is configured to absorb heat generated by the scanning imaging component in operation;

the imaging module is configured to reconstruct a spatial distribution image of a physical feature of the magnetic particles; and the control device is configured to control, according to set control instructions, current changes of the rotating scanning module and an excitation coil of the scanning imaging component, a mechanical rotation speed of the rotating scanning module of the scanning imaging component, a depth of movement of the examination bed, and a hydraulic pressure of the cooling system, such that the field-free point performs layer-by-layer scanning through translation and rotation, thereby achieving scanning imaging of the examination object.

3. The human-scale closed-bore MPI device based on the radial-Cartesian trajectory scanning according to claim 2, wherein the direction of the central axes of the two circular permanent magnets is taken as an x direction, and the vertical direction perpendicular to the x axis is taken as a z direction.

4. The human-scale closed-bore MPI device based on the radial-Cartesian trajectory scanning according to claim 2, wherein residual magnetization directions of the two circular permanent magnets are opposite to each other and parallel to the central axes of the two circular permanent magnets.

5. The human-scale closed-bore MPI device based on the radial-Cartesian trajectory scanning according to claim 4, wherein output voltage phases of the third cylindrical coil and the fourth cylindrical coil are opposite.

6. A human-scale closed-bore MPI method based on a radial-Cartesian trajectory scanning, implemented through the human-scale closed-bore MPI device based on the radial-Cartesian trajectory scanning according to claim 5, and comprising:

S100: moving the examination object along the axial direction of the imaging hole to the preset position;

S200: constructing, based on the two circular permanent magnets, the two curved rectangular coils, and the first cylindrical coil, the field-free point and a dynamic magnetic field for radial-Cartesian trajectory scanning;

S300: acquiring, based on the second cylindrical coil, the third cylindrical coil, and the fourth cylindrical coil, the nonlinear magnetization response signal of the magnetic particles;

S400: reconstructing, based on the acquired nonlinear magnetization response signal of the magnetic particles, the spatial distribution image of the physical feature of the magnetic particles through a preset imaging algorithm; and S500: moving the examination object along the axial direction of the imaging hole, and repeating steps S200 to S400 until the imaging of all examination regions of the examination object is completed.

7. The human-scale closed-bore MPI method based on the radial-Cartesian trajectory scanning according to claim 6, wherein the operation of constructing the field-free point and the dynamic magnetic field for the radial-Cartesian trajectory scanning comprises:

keeping the two circular permanent magnets and the first cylindrical coil fixed; and controlling the two curved rectangular coils to rotate uniformly and mechanically around the central axes of the two circular permanent magnets; applying alternating currents of same magnitude and direction to the two curved rectangular coils; and applying an alternating current to the first cylindrical coil;

wherein, a frequency of the alternating current applied to the first cylindrical coil is at least N times a frequency of the alternating current applied to the two curved rectangular coils; and the frequency of the alternating current applied to the two curved rectangular coils is at least N times a mechanical rotation frequency of the two curved rectangular coils.

8. The human-scale closed-bore MPI method based on the radial-Cartesian trajectory scanning according to claim 6, wherein the operation of acquiring, based on the second cylindrical coil, the third cylindrical coil, and the fourth cylindrical coil, the nonlinear magnetization response signal of the magnetic particles comprises: connecting the second cylindrical coil and the fourth cylindrical coil in series to output a voltage signal for filtering, noise reduction, and amplification, thereby acquiring the nonlinear magnetization response signal of the magnetic particles.

* * * * *